United States Patent [19]

Miyagi et al.

[11] Patent Number: 5,729,646
[45] Date of Patent: Mar. 17, 1998

[54] OPTICAL HOLLOW WAVEGUIDE, METHOD FOR FABRICATING THE SAME, AND LASER TRANSMISSION APPARATUS USING THE SAME

[75] Inventors: Mitsunobu Miyagi, 3-32, Sunaoshi-machi, Taihaku-ku, Sendai-shi, Miyagi-ken; Yuji Kato, Miyagi-Ken; Akihito Hongo, Ibaraki-Ken; Yoshihide Okagami, Kyoto-Fu, all of Japan

[73] Assignees: Hitachi Cable Ltd., Tokyo; Mitsunobu Miyagi, Miyagi-Ken; J. Morita Manugaciturimg Corporation, Kyoto-Fu, all of Japan

[21] Appl. No.: 783,195

[22] Filed: Jan. 15, 1997

Related U.S. Application Data

[63] Continuation of Ser. No. 422,564, Apr. 14, 1995, abandoned.

[30] Foreign Application Priority Data

| Apr. 15, 1994 | [JP] | Japan | 6-113339 |
| Feb. 27, 1995 | [JP] | Japan | 7-038129 |

[51] Int. Cl.⁶ .................................................. G02B 6/02
[52] U.S. Cl. ............................ 385/125; 385/141; 385/143
[58] Field of Search ........................................ 385/125, 126, 385/123, 124, 141, 142, 143, 144, 145

[56] References Cited

U.S. PATENT DOCUMENTS

| 5,276,761 | 1/1994 | Shimoyama et al. | 385/125 |
| 5,497,440 | 3/1996 | Croitoru et al. | 385/125 |
| 5,497,441 | 3/1996 | Croitoru et al. | 385/125 |

*Primary Examiner*—Phan T. H. Palmer
*Attorney, Agent, or Firm*—Helfgott & Karas, P C.

[57] ABSTRACT

A polyimide resin layer is formed on an inner surface of a metal pipe or a non-metallic pipe having a metal thin film on an inner surface to provide an optical hollow waveguide. The polyimide resin layer is transparent relative to a wavelength band of a laser light transmitted through the optical hollow waveguide. The optical hollow waveguide is fabricated by supplying solution of polyimide precursor to a hollow internal of the metal pipe or the non-metallic pipe, and heating and drying the solution to provide a polyimide resin layer. The solution-supplying step and the solution-heating and drying step are repeated to increase a thickness of the polyimide resin layer up to a predetermined value.

16 Claims, 6 Drawing Sheets

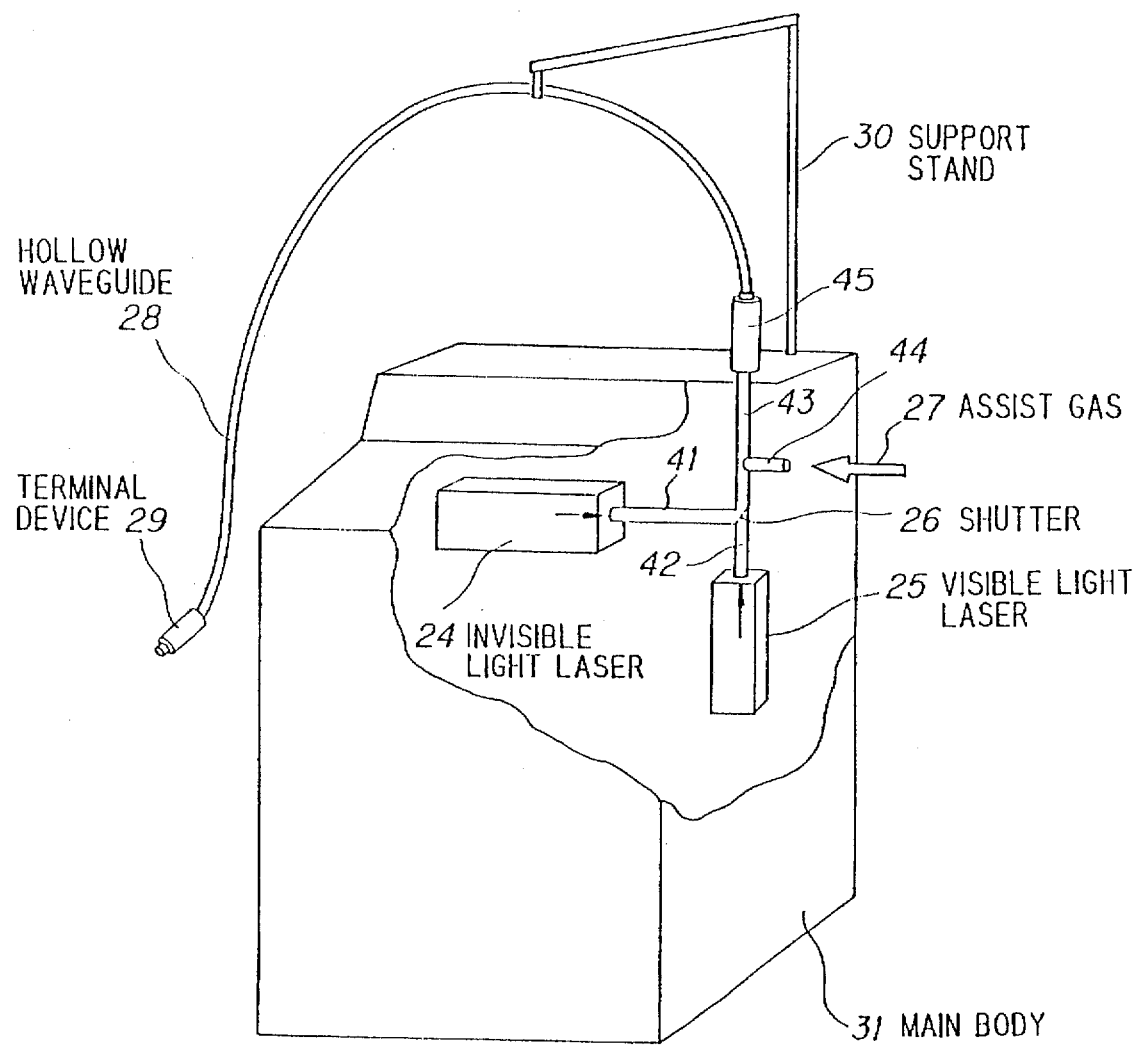

OPTICAL HOLLOW WAVEGUIDE, METHOD FOR FABRICATING THE SAME, AND LASER TRANSMISSION APPARATUS USING THE SAME

This is a continuation of application Ser. No. 08/422,564, filed Apr. 14, 1995 now abandoned.

FIELD OF THE INVENTION

The invention relates to an optical hollow waveguide, a method for fabricating the same, and a laser transmission apparatus using the same, and more particularly, to an optical hollow waveguide with improved flexibility and wide band transmission properties covering an infrared wavelength band, a visible wavelength band, and an ultraviolet wavelength band, a method for fabricating the optical hollow waveguide, and a laser transmission apparatus using the optical hollow waveguide.

BACKGROUND OF THE INVENTION

Infrared light having a wavelength of more than 2 μm is used in various fields such as medical treatment, industrial process, measurement, chemical industries, etc. Especially, Er-YAG (erbium-yttrium-aluminium-garnet) laser having a wavelength band of 2.9 μm, CO (carbon monooxide gas) laser having a wavelength band of 5 μm, and $CO_2$ (carbon dioxide gas) laser having a wavelength band of 10.6 μm provide high output powers, because these lasers have high lasing efficiency, and these lasers are extremely important for light sources for devices for medical treatment, industrial process, etc., because large absorption is obtained relative to water.

A conventional quartz-optical fiber which is used for optical communication is very high in loss due to infrared absorption caused by molecular oscillation or vibration at a wavelength of more than 2 μm. Therefore, the quartz-optical fiber is difficult to be used for a waveguide for transmitting laser light at the infrared wavelength band. For this reason, new types of optical waveguides which can be used at the infrared wavelength band to broaden the applicable fields have been intensively researched and developed.

The optical waveguides used at the infrared wavelength band having a wavelength of more than 2 μm are classified into two types, wherein the first type is an infrared optical fiber having a solid core, and the second type is an optical hollow waveguide.

For materials of the infrared optical fibers, heavy metal oxide glass such as $GeO_2$, $GeO_2$-$Sb_3O_3$, etc, chalcogenide glass such as As-S, As-Se, etc., and halogenide are mainly used, wherein the halogenide is classified into halide glass such as $ZnCl_2$, $CdF_3$-$BaF_2$-$ZrF_4$, etc., and crystalline metal halogenide such as KRS-5 (mixed crystal of TlBr and TlI), AgCl, AgBr, KCl, etc.

On the other hand, optical hollow waveguides of various structures, materials, configurations, etc. have been proposed and tentatively fabricated. Among the optical hollow waveguides, a metal hollow waveguide comprising a metal pipe, and a high reflection layer which is a dielectric layer formed on an inner surface of the metal pipe is applied to a laser processsing apparatus of a large electric power, wherein the dielectric layer is of germanium, zinc sulfide, etc., and the metal pipe is of nickel, etc.

In fabricating the optical hollow waveguide, a thin inorganic dielectric film of germanium or zinc sulfide which is transparent for lights at the infrared wavelength band is formed on an aluminum pipe by sputtering, and a thick nickel layer is formed on the thin inorganic dielectric film. Then, the aluminium pipe is removed to provide the optical hollow waveguide by chemical etching.

The optical hollow waveguide may comprise a thin silver film between the thin dielectric film and the thick nickel pipe to lower transmission loss. In this optical hollow waveguide, it is confirmed that a transmission loss of 0.05 dβ/m and a transmission capacity of 3 kW are obtained to transmit a sufficient energy of laser light, so that metal plate members can be cut and welded. Such optical hollow waveguides have advantages as compared to infrared optical fibers having solid cores in that less reflection occurs at input and output ends, and cooling efficiency is high to allow the transmission of a large electric power.

In the field of chemical laser, a light source such as Excimer laser, etc. is used at the ultraviolet wavelength band. When an optical fiber having a solid core is used at this band, however, loss is sharply increased due to Rayleigh scattering as a wavelength of a laser light is decreased. For this reason, the optical fiber can not be used for a transmission line at this band. An optical hollow waveguide having an inner layer of germanium or zinc sulfide can not be also used at the ultraviolet wavelength band, because germanium or zinc sulfide is opaque for ultraviolet lights. In this respect, $CaF_2$ and fluorine resin which are transparent for ultraviolet lights may be used for an inner layer of an optical hollow waveguide. However, it is very difficult for $CaF_2$ and fluorine resin to be deposited as an inner layer of an optical hollow waveguide in accordance with a thickness precision, a uniformity, a surface roughness, etc. For this reason, the research and the development of optical hollow waveguides have not been put forward at the ultraviolet wavelength band.

Here, disadvantages of the above described optical fibers and optical hollow waveguides will be explained below.

(1) In an optical fiber having a solid core to be used at the infrared wavelength band, the transmission of a large electric power is difficult due to reflection loss at input and output ends, because the optical fiber is fabricated from materials of high refractive indices. Especially, the aforementioned hyaline-materials are generally of low melting and softening points to result in damages at the input and output ends, even if the reflection loss is small. Further, an optical fiber of a hyaline-material selected from available hyaline-materials transmits only a light having a wavelength of less than 6 to 7 μm at the infrared wavelength band, and is difficult to transmit a light of a $CO_2$ laser having a wavelength of 10.6 μm.

(2) In some of crystalline infrared optical fibers, a transmission band including a wavelength of 10.6 μm for a $CO_2$ laser light is obtained. However, the crystalline infrared optical fibers are low in reliability for a long operative period in that plasticity deformation occurs due to repeated bendings, and deliquescence is large.

(3) In an optional hollow waveguide having an inner layer of an inorganic material, the fabrication process is complicated to lower productivity and to make it difficult that size is made small and length is made large. Practically, a length of the optical hollow waveguide is several meters at most, because the fabrication process comprises a step of sputtering, and an inner diameter of the optical hollow waveguide ranges 0.8 to 1 mm at most, because it is equal to an outer diameter of an aluminum pipe to be etched after the formation of the inner layer thereon. The optical hollow waveguide is difficult to be bent as the size thereof is increased. As a result, a bending loss is increased in the optical hollow waveguide. Further a laser light including several high order modes is propagated through the optical hollow waveguide to deteriorate light-focusing properties.

(4) At the ultraviolet wavelength band, the loss of an ordinary optical fiber is extremely high due to the increase of loss caused by Rayleigh scattering. For this reason, an optical hollow waveguide is advantageous to be used at this band. However, a fabrication process of an optical hollow waveguide using a dielectric material applicable to the transmission of ultraviolet lights has not been established as described before.

SUMMARY OF THE INVENTION

Accordingly, it is an object of the invention to provide an optical hollow waveguide in which laser lights are transmitted with low losses at a wide wavelength band, and to provide a method for fabricating the same and a laser transmission apparatus using the same.

It is a further object of the invention to provide an optical hollow waveguide which is improved in productivity and reliability, and to provide a method for fabricating the same and a laser transmission apparatus using the same.

According to the first aspect of the invention, an optical hollow waveguide, comprises:

a hollow pipe member; and a polyimide resin layer formed on an inner resin surface of the hollow pipe member, the polyimide layer being transparent relative to a wavelength band of a transmission light of the optical hollow waveguide.

According to the second aspect of the invention, a method for fabricating an optical hollow waveguide, comprises the steps of:

supplying solution of polyimide precursor at least on an inner surface of a hollow pipe member, the hollow pipe member being of a metal at least on the inner surface by a predetermined thickness;

heating and drying the solution of polyimide precursor supplied on the inner surface of the hollow pipe member to provide a polyimide resin layer; and repeating the steps of supplying, and heating and drying to increase a thickness of the polyimide resin layer up to a predetermined value.

According to the third aspect of the invention, a laser transmission apparatus using an optical hollow waveguide, comprises:

means for emitting a laser light;

means for transmitting the laser light; and means for coupling the emitting means to the transmitting means;

wherein the transmitting means is the optical hollow waveguide, the optical hollow waveguide comprising a hollow pipe member, and a polyimide resin layer formed on an inner surface of the hollow pipe member, the hollow pipe member being of a metal at least on the inner surface by a predetermined thickness, and the polyimide resin layer being transparent relative to the laser light.

BRIEF DESCRIPTION OF THE DRAWINGS

The invention will be explained in more detail in conjunction with appended drawings, wherein:

FIG. 7 is an explanatory diagram showing a laser transmission apparatus using the optical hollow waveguide as shown in FIG. 1.

DESCRIPTION OF THE PREFERRED EMBODIMENTS

Figure 1:
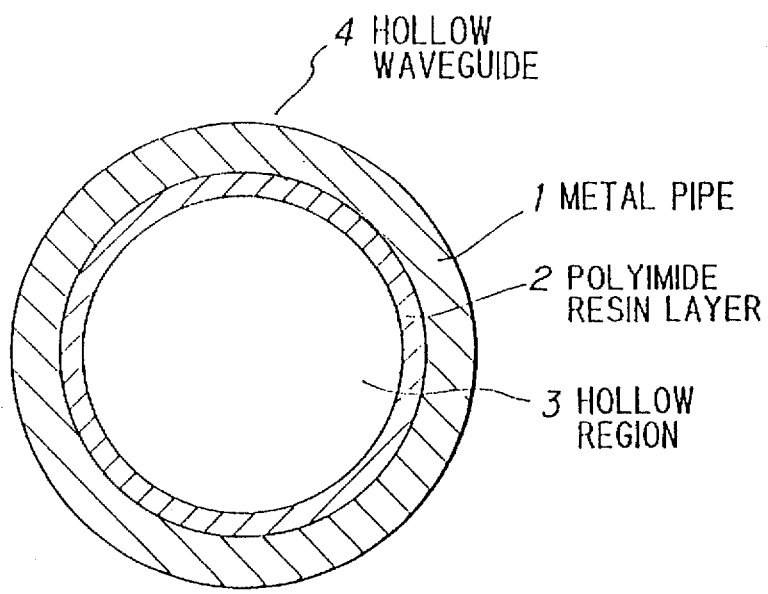
FIGS. 1 to 3 are cross-sectional views showing optical hollow waveguides in first to third preferred embodiments according to the invention.

FIG. 1 shows an optical hollow waveguide 4 in the first preferred embodiment according to the invention. The optical hollow waveguide 4 comprises a metal pipe 1, and a polyimide resin layer 2 provided on an inner surface of the metal pipe 1, wherein a hollow region 3 is defined by the polyimide resin layer 2.

In operation, a laser light is repeatedly reflected on the inner surface of the polyimide resin layer 2 and at an interface between the polyimide resin layer 2 and the metal pipe 1, so that the laser light is transmitted through the optical hollow waveguide 4.

In this optical hollow waveguide 4, an energy of the laser light is not permeated deeply into the metal pipe 1, because light is well absorbed in general by metals. Therefore, the metal pipe 1 may be as thin as a skin depth from the optical view point. For this reason, a thickness of the metal pipe 1 is determined depending on a mechanical strength of the optical hollow waveguide 4. When a metal having a large absolute value of a complex index of refraction such as Ag, Au, etc. is preferable to be used for the metal pipe 1 in lowering a transmission loss. However, such a metal is not practical to be used for the metal pipe 1 from the economical and mechanical view points.

The metal pipe 1 may be a composite metal pipe comprising an outer metal pipe and an inner thin metal film, wherein the outer metal pipe may be a phosphor bronze pipe having a resistance to plasticity-deformation caused by bending, or a stainless steel pipe having chemical stability and a small surface roughness on the inner surface thereof, and the inner thin metal film may be a gold, silver or copper film having a large absolute value of a complex index of refraction, or a nickel film having a large adherence force obtained by non-electrolytic plating. In this case, the inner metal film may be as thin as a skin depth or more than that.

The polyimide resin layer 2 is a resin material which is low in refractive index is transparent at a wide wavelength band covering ultraviolet to infrared light regions. This kind of polyimide resin has a plurality of absorption peaks inherent to organic materials which debunch relative to a wavelength of a transmitted light, wherein wavelengths of the absorption peaks are not coincident to lasing wavelengths of practically important lasers such as Er-YAG laser, CO laser, $CO_2$ laser, etc.

Even at a wavelength band other than a wavelength band having the absorption peaks inherent to materials at the infrared wavelength band, an absorption coefficient of polyimide resin is large as compared to an inorganic material such as germanium, zinc sulfide, etc. In the optical hollow waveguide, however, almost all of a laser light energy is transmitted through the hollow region 3, while a very small portion thereof is transmitted through the polyimide resin layer 2, so that a transmission loss is extremely small. This is quite different from an optical fiber having a solid core for transmitting a laser light energy.

As described on page 1510 of "IEEE J. Quantum Electron, Vol 26, 1990" by A. Hongo, K. Morosawa, T. Shiota, Y. Matsuura, and M. Miyagi, it is known that a transmission loss becomes small in an optical hollow waveguide, as a refractive index of a dielectric thin film provided on an inner surface of a metal pipe becomes proximate to a value of $2^{1/2}$. In this regard, refractive indices of germanium and zinc sulfide which are conventionally used for the inner dielectric film are 4.0 and 2.3, respectively, while that of the polyimide resin layer 2 which is used in the first preferred embodiment is approximately 1.5 to 1.6 to provide the optical hollow waveguide 4 having a lower transmission loss. When a refractive index is made small, a tolerance on a thickness of an inner dielectric layer becomes large to make the fabrication of an optical hollow waveguide easier. The inventors have confirmed that polyimide resin has an ideal refractive index for the reason as described above.

The most important advantage in using polyimide resin in the first preferred embodiment is that it has heat-proof properties. A small portion of a laser light energy which is transmitted through the polyimide resin layer 2 is partially absorbed to be converted to heat. Therefore, the heat-proof properties are very important for the optical hollow waveguide 4 for transmitting a laser light of a large energy. Although materials having low refractive indices and low absorption coefficients are found other than polyimide resin, there is a possibility in which the increase of a transmission loss is caused, and harmful substances are generated, respectively, by thermal deformation or thermal decomposition of such materials. On the other hand, polyimide resin has a glass-transition point of more than 320° C. and a thermal decomposition temperature of more than 500° C. to provide excellent heat-proof properties. In accordance with these properties, polyimide resin is most appropriate for the transmission of a laser light.

A refractive index of polyimide resin can be more proximate to the ideal value of $2^{1/2}$ in accordance with the suppression of CH radical-absorption loss and the decrease of refractive index by substituting fluorine for a portion of polyimide resin. Further, hygroscopicity of polyimide resin is decreased to enhance reliability for a long operative period, and is very important, especially, for the transmission of infrared lights, because absorption caused by OH radicals is observed at the infrared wavelength band. In this point, however, over-substitution of fluorine must be avoided, because it results in the deterioration of heat-proof properties, the increase of a linear expansion coefficient, and the decrease of an adherence force.

In accordance with the above discussion, the inventors have confirmed that polyimide resin including fluorine of 20 to 35 weight % is appropriate for the polyimide resin layer 2 of the optical hollow waveguide 4. For instance, when polyimide resin includes fluorine of 35 weight %, a refractive index thereof is approximately 1.5 at the infrared wavelength band, and a glass-transition point of 320° C. and a thermal decomposition temperature of 500° C. are maintained therein. In addition, this fluorine-included polyimide resin is decreased in hygroscopicity to be less than approximately one fifth as compared to polyimide resin including no fluorine.

Figure 2:
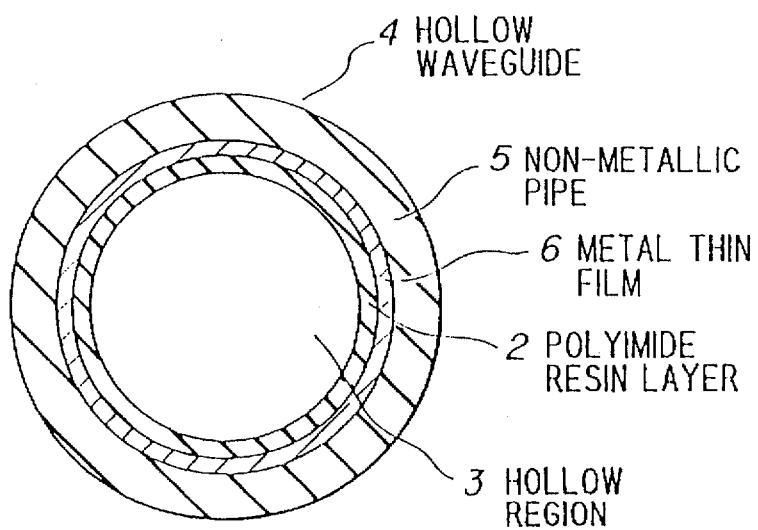

FIG. 2 shows an optical hollow waveguide in the second preferred embodiment according to the invention. The optical hollow waveguide comprises a non-metallic pipe 5 such as a fluorine resin pipe, a silicon resin pipe, a glass pipe, etc., a metal thin film 6 provided on a inner surface of the non-metallic pipe 6, and a polyimide resin layer 2 provided on an inner surface of the metal thin film 6.

The fluorine resin pipe and the silicon resin pipe for the non-metallic pipe 5 provide flexibility and anti-medicine property, and the glass pipe for the on-metallic pipe 5 is effective to decrease a transmission loss, because it has a very small surface roughness. Especially, a quartz glass pipe is easy to provide an optical hollow waveguide which is much longer than one using other materials in addition to the excellent anti-medicine property. The mechanical strength of glass pipes is remarkably enhanced by coating resin thereon, so that the resin-coated glass pipes can be bent even by a small bending radius.

For the metal thin film 6, gold, silver or copper having a large absolute value of complex index of refraction, or molybdenum which is hard and difficult to be damaged is appropriate to be used. For the optical purpose, one layer of a metal film is sufficient for the metal thin film 6. In increasing an adherence force of the metal thin film 6 to the non-metallic pipe 5, an intermediate metal film such as a nickel film may be provided between the non-metallic pipe 5 and the metal thin film 6. In such a case, non-electrolytic plating solution is supplied from one end of the non-metallic pipe 5 therethrough to the other end thereof, so that a nickel film having a high adherence force is deposited on the whole inner surface of the non-metallic pipe 5.

The intermediate metal film is preferable to be less than 50 μm in thickness. When the intermediate metal film has a thickness of more than 50 μm, adherence force tends to lower due to the differences of internal stress and linear expansion coefficient from those of the metal thin film 6.

Figure 3:
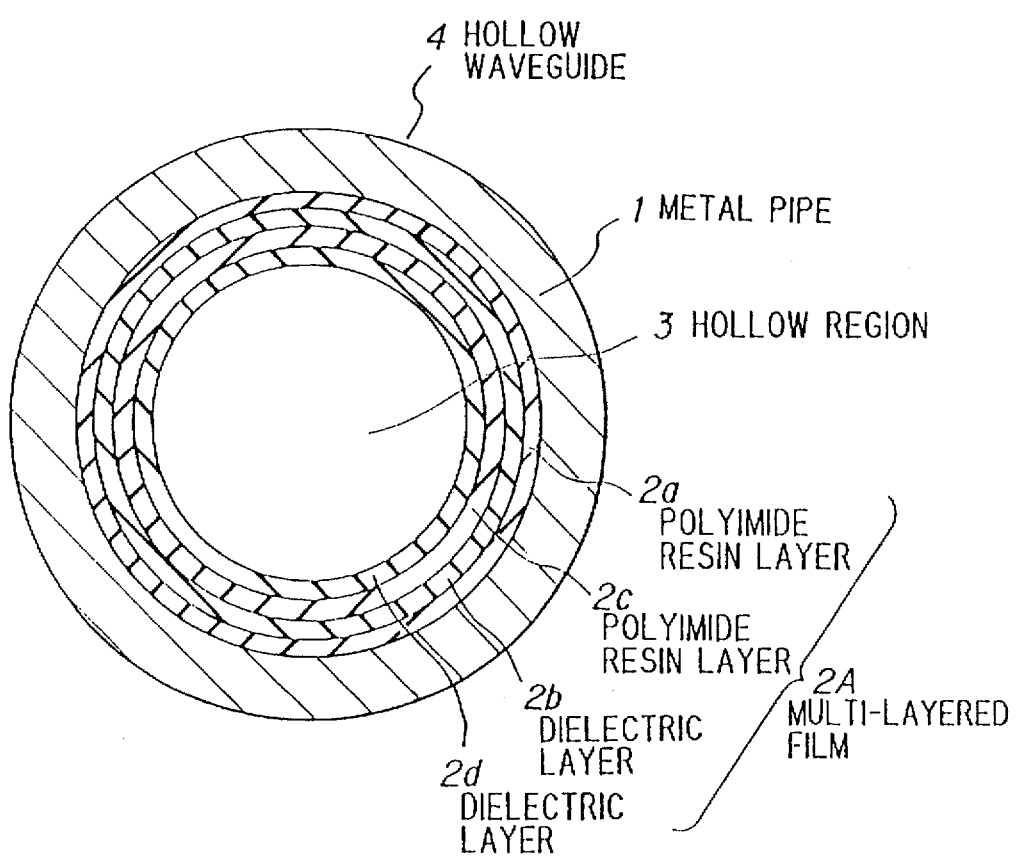

FIG. 3 shows an optical hollow waveguide 4 in the third preferred embodiment according to the invention. The optical hollow waveguide 4 comprises a metal pipe 1, and a multi-layered film 2A composed of polyimide resin layers 2a and 2c having an equal refractive index and dielectric layers 2b and 2d having a second refractive index, wherein a hollow region is defined by the multi-layered film 2A. In this optical hollow waveguide 4, the decrease of transmission loss is realized as the difference of the first and second refractive indices is increased, and the layer-number of the multi-layered film 2A is increased. The polyimide layers 2a and 2c can be changed in refractive index by changing a content of fluorine, and the dielectric layers 2b and 2d may be of an inorganic or organic material which is transparent and has a refractive index different from that of the polyimide layers 2a and 2c, and may be of polyimide resin having a refractive index different from that of the polyimide resin layers 2a and 2c. In case where the first to fourth layers 2a to 2d of the multi-layered film 2 are of polyimide resin, reliability is increased, because adherence among the first to fourth layers 2a to 2d is enhanced.

The dielectric layers 2b and 2d may be of an inorganic dielectric material such as germanium, zinc sulfide, silver iodide, etc. which is transparent at the infrared wavelength band and has a refractive index higher than that of polyimide resin. A thin film of silver iodide is easily deposited on an inner surface of a pipe by forming a silver thin film on the inner surface of the pipe, and chemically iodizing the silver thin film.

In the third preferred embodiment, a polyimide layer may be further provided on the inner surface of the dielectric layer 2d. The order of each layer is determined in the multi-layered film 2A dependently on the refractive indices and the thicknesses of each layer.

Figure 4:
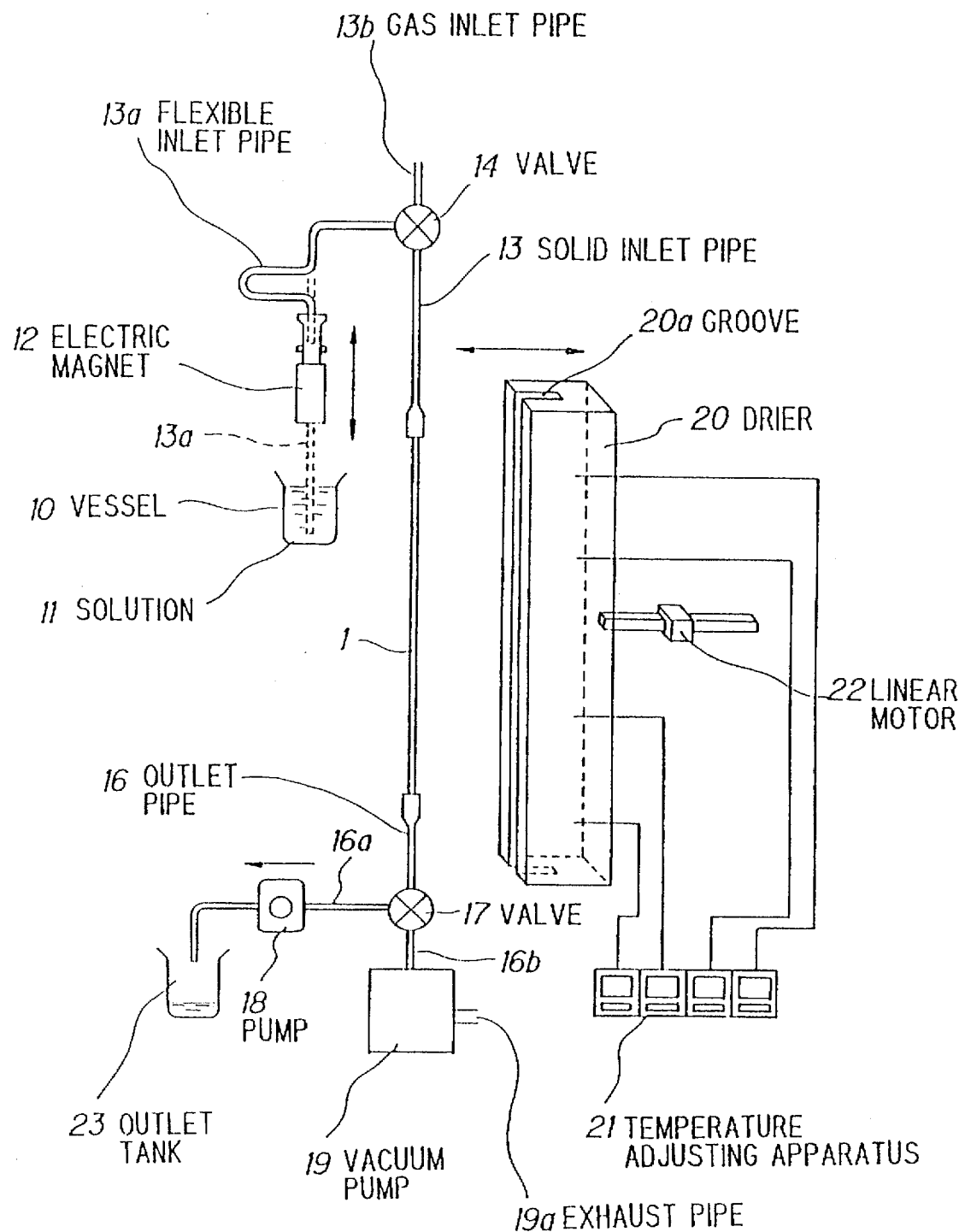
FIG. 4 is an explanatory diagram showing an apparatus for fabricating the optical hollow waveguide as shown in FIG. 1.

FIG. 4 shows an apparatus for fabricating the optical hollow waveguide as shown in FIG. 1.

Solution of polyimide precursor is diluted to be supplied into the pipe 1 by solvent of dimethylacetamide or N-methyl-2-pyrrolidon, so that the polyimide resin layer 2 is formed on the inner surface of the metal pipe 1, wherein a thickness of the polyimide resin layer 2 is controlled in accordance with the condition of a resin content, viscosity, etc.

In the apparatus as shown in FIG. 4, the solution 11 of polyimide precursor diluted by the solvent is contained in a vessel 10. The solution 11 is, for instance, "Torayneece" manufactured by Toray Industries, Inc. in Tokyo, Japan, or "OPI" manufactured by Hitachi Chemical Co., Ltd. in Tokyo, Japan. An electric magnet 12 is provided on the vessel 10 to rise and lower a flexible solution inlet pipe 13a which is connected via a three-port valve 14 to a solid solution inlet pipe 13. The metal pipe 1 is detachably connected at one end thereof to one end of the solid inlet pipe 13, and at the other end to a solution outlet pipe 16, respectively. The solution outlet pipe 16 is divided into first and second outlet pipes 16a and 16b by a three-part valve 17. The first outlet pipe 16a is communicated to an outlet tank 23 and is provided with a pump 18, and the second outlet pipe 16b is connected to a vacuum pump 19 having an exhaust pipe 19a.

A drier 20 is provided to face the metal pipe 1, and controlled by a temperature-adjusting apparatus 21. The drier 20 is driven to move in an arrow-direction by a linear motor 22, so that the metal pipe 1 is surrounded by walls of a groove 20a vertically provided along the drier 20. The three-port valve 14 is connected to a gas inlet pipe 13b.

In operation, the three-port valve 14 is turned on the side of the flexible solution inlet pipe 13a which is then lowered by the electric magnet 12 driven by a power supply (not shown). Thus, the lower end of the flexible solution inlet pipe 13a is immersed into the solution 11 of polyimide precursor contained in the vessel 10. Then, the pump 18 is driven to draw the solution 11 which is flown from the three-port valve 14 via the solid solution inlet pipe 13, the metal pipe 1 and the solution outlet pipe 16 to the three-port valve 17. After the solution 11 is flown inside the metal pipe 1, the electric magnet 12 is turned off, so that the lower end of the flexible solution inlet pipe 13a is risen up to be left from the upper surface of the solution 11 contained in the vessel 10. Thus, the solution 11 is exhausted from the inside of the metal pipe 1 via the solution outlet pump 16 and the three-port valve 17 to the outlet tank 23. After finishing the exhaust of the solution 11 from the metal pipe 1, the pump 18 is stopped to be driven, and the linear motor 22 is driven to move the drier 20 in the arrow-direction, so that the metal pipe 1 is surrounded by the walls of the groove 20a of the drier 20. The drier 20 is controlled to maintain the temperature at 100° C. by the temperature adjusting apparatus 21, and a process for drying the metal pipe 1 is carried out for 10 minutes by the drier 20. Consequently, the solvent is evaporated from the solution 11 of polyimide precursor supplied on the inner surface of the metal pipe 1, so that the polyimide resin layer 2 as shown in FIG. 1 is formed thereon. Prior to the drying process, the three-port valve 14 is turned on the side of the gas inlet pipe 13b, and the three-port valve 17 is turned on the side of the vacuum pump 19. Then, inert gas such as nitrogen, argon, helium, etc. is supplied from the gas inlet pipe 13b to the metal pipe 1, and the vacuum pump 19 is driven to draw the inert gas to the exhaust pipe 19a. Thus, the dehydration and the drying of the polyimide resin layer 2 is completed. Thereafter, the linear motor 22 is driven to move the drier 20 back to the home position.

In accordance with the use of polyimide precursor solution adjusted in viscosity and resin content, a polyimide resin layer is easily formed on an inner surface of an optical hollow waveguide with a predetermined thickness, even if an inner diameter of the optical hollow waveguide is as small as approximately 200 to 500 μm or less, and is as large as 1 mm or more.

Figure 5:
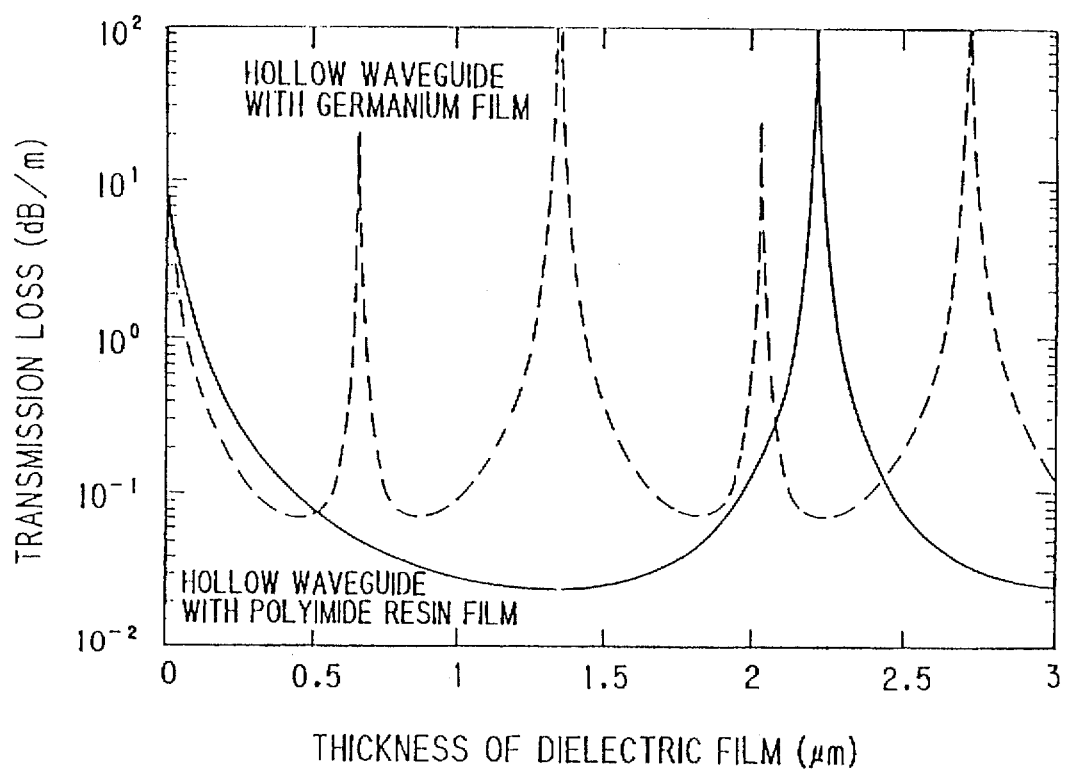
FIG. 5 is a graph showing a transmission loss relative to a thickness of an inner layer of the optical hollow waveguide as shown in FIG. 1.

FIG. 5 shows a transmission loss relative to a thickness in a range of 0 to 3.0 microns of an inner dielectric layer of an optical hollow waveguide, wherein a silver hollow waveguide with a polyimide resin inner layer having an inner diameter of 800 μm and a refractive index of as low as 1.5 to 1.6 and a conventional silver hollow waveguide with a germanium inner layer having an inner diameter of 800 μm and a refractive index of 4 are compared in transmitting a $CO_2$ laser light of $HE_{11}$ mode having a wavelength of 10.6 μm.

In the silver hollow waveguide having the polyimide resin inner layer which is an optical hollow waveguide in the invention, the minimum transmission loss is decreased to be one-thirds of that in the conventional silver hollow waveguide with a germanium inner layer by selecting a thickness of the polyimide resin inner layer to be approximately 1.4 μm. As apparent from the graph, the transmission losses of the hollow waveguides in the invention and the conventional structure change with periods depending on materials on the inner layers, wherein the invention is much longer in period than the conventional structure, so that a tolerance of a thickness for an inner layer becomes wider in the invention. The above described optimum thickness is changed dependently on a wavelength of a transmitted laser light. Pot this reason, an optical hollow waveguide of a low transmission loss is fabricated for any laser lights including a $Co_2$ laser light by setting a thickness of a dielectric inner layer to be optimum relative to a wavelength of a transmission laser light excluding an absorption band of polyimide resin.

Figure 6:
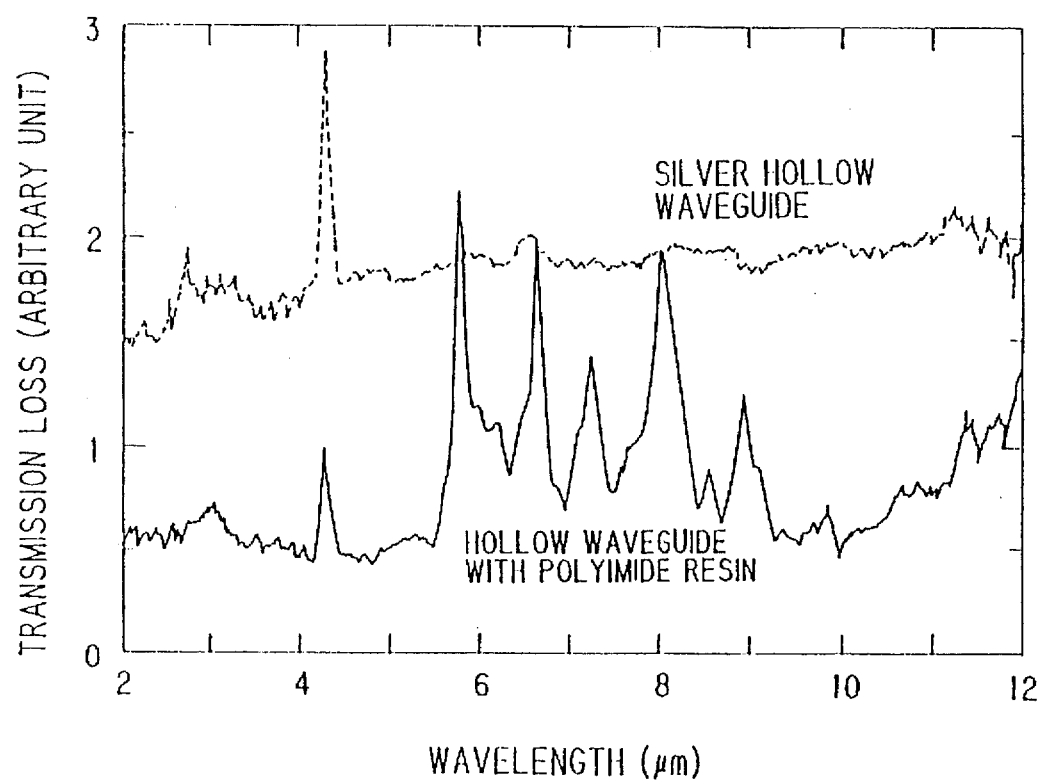
FIG. 6 is a graph showing a transmission loss relative to a wavelength of a light transmitted through the optical hollow waveguide as shown in FIG. 1.

FIG. 6 shows a transmission loss of a light transmitted through a silver hollow waveguide having a polyimide resin inner layer relative to a wavelength of a light, wherein a transmission loss of a light transmitted through a silver hollow waveguide having no polyimide resin inner layer is also shown for comparison with that of the silver hollow waveguide having the polyimide resin inner layer. As apparent from the graph, there are several absorption peaks inherent to polyimide resin at a wavelength band of 6 to 9 μm. However, no absorption peak is found at lasing wavelength bands including a lasing wavelength of 2.9 μm for an Er-YAG laser, that of 5 μm for a CO laser, and that of 10.6 μm for a $CO_2$ laser which are important in practical. Therefore, the low loss transmission of lights for these lasers can be carried out.

In the optical hollow waveguides in the first to third preferred embodiments according to the invention, a visible light of a He-Ne laser may be combined with one or more of the aforementioned laser lights, so that one or more of the laser lights are switched over to be transmitted therethrough. This is effective to ensure safety, because invisible laser light is made visible. Further, dried air, nitrogen gas, carbon dioxide gas, etc. can be advantageously supplied into the optical hollow waveguides by using the hollow regions 3.

This avoids the invasion of dusts, and water, and helps an optical hollow waveguide to be cooled.

In the field of medical treatment, it is required to supply a diseased part with assist gas such as air, nitrogen gas, carbon dioxide gas, etc., to be described later. For this purpose, an optical hollow waveguide is used to provide a laser transmission apparatus as shown in FIG. 7.

In the laser transmission apparatus, an invisible light laser 24 such a $CO_2$ laser, an Er-YAG laser, an Excimer laser, etc. and a visible light laser 25 such as a He-Ne laser, etc. are provided in a main body 31, and the invisible light laser 24 and the visible light laser 25 are coupled to light paths 41 and 42, respectively, which are coupled to a light path 43, wherein an optical shutter 26 is provided at a coupling point of the light paths 41, 42 and 43, and a gas inlet 44 for supplying assist gas 27 to the light path 43 is connected to the light path 43. An optical hollow waveguide 28 as explained in the first to third embodiments is supported to be coupled via an optical coupler 45 to the light path 43 by a support stand 30, and the optical hollow waveguide 28 is provided at an output end thereof with a terminal device 29 including a focusing lens (not shown), etc.

In operation, the optical shutter 26 is controlled to take a posture for shutting the light path 41 for the invisible light laser 24, and for coupling the light path 42 for the visible light laser 25 to the light path 43. In this state, the terminal device 29 is positioned in the vicinity of a diseased part of a patient and a radiated light is focused on the diseased part by observing a visible light which is emitted from the visible light laser 25 and radiated from the terminal device 29 to the patient. Then, the shutter 26 is controlled to take a posture for shutting the light path 42 for the visible light laser 25, and for coupling the light path 41 for the invisible light laser 24 to the light path 43. Thus, an invisible light is radiated from the invisible light laser 24 via the light paths 41 and 43 and the optical hollow waveguide 28 to the diseased part by the terminal device 29. If necessary, the assist gas is supplied to the gas inlet 44, so that the assist gas is introduced into the optical hollow waveguide 28.

In the laser transmission apparatus, the shutter 26 may be replaced by a beam combiner which reflects an invisible light and transmits a visible light. In such a case, the beam combiner is positioned to be slant at the coupling point by 45°, so that the visible and invisible lights are switched over or superposed by turning the visible and invisible light lasers 24 and 25 on and off.

The inventors have confirmed in experiments that the laser transmission apparatus is well applied to a surgery operation using a laser cutting instrument or scalpel in which the radiation of a $CO_2$ laser light is effective for the refraining of blocking. On the other hand, a Er-YAG laser light is appropriate to be used for cutting hard tissues such as teeth, bones, etc. In the above experiments, an optical hollow waveguide having a length of 1 m, an inner diameter of 700 μm, and an outer diameter of 850 μm is used, and expected results are obtained in the drilling operation using the $CO_2$ laser light and the cutting of teeth using the Er-YAG laser light. Especially, a transmission factor of more than 80% and an input power of 300 mJ (10PPS) are obtained in transmitting the Er-YAG laser light. The Er-YAG laser is evaluated for dental treatment in place of a drill connected to an air turbine. For this purpose, the optical hollow waveguides in the first to third preferred embodiments are advantageously used for transmitting the Er-YAG laser light.

In the invention as described above, a polyimide layer formed on an inner surface of a metal pipe or a non-metallic pipe having an inner metal thin film provides transparency relative to a wide wavelength band covering infrared to ultraviolet wavelengths, and has an ideal refractive index, so than only a small amount of light is absorbed to provide a low loss transmission. Even more, polyimide resin has high heat-proof and anti-hygroscopicity properties. Therefore, an optical hollow waveguide transmits a large electric power of a laser light with the highest reliability.

Although the invention has been described with respect to specific embodiment for complete and clear disclosure, the appended claims are not to be thus limited but are to be construed as embodying all modification and alternative constructions that may occur to one skilled in the art which fairly fall within the basic teaching herein set forth.

What is claimed is:

1. An optical hollow waveguide operational over a transmission wavelength band extending from ultraviolet to infrared light regions, comprising:

a hollow pipe member providing structural support; and a polyimide resin film less than ten microns thick formed on an inner surface of said hollow pipe member, said polyimide resin layer being transparent relative to said wavelength band of a transmission light of said optical hollow waveguide.

2. An optical hollow waveguide operational over a transmission wavelength band extending from ultraviolet to infrared light regions, comprising:

a hollow pipe member providing structural support and having a metal film at least on an inner surface thereof; and a polyimide resin layer less than ten microns thick formed on an inner surface of said metal film of said hollow pipe member, said polyimide resin layer being transparent relative to said wavelength band of a transmission light of said optical hollow waveguide.

3. An optical hollow waveguide operational over a transmission wavelength band extending from ultraviolet to infrared light regions, comprising:

a hollow pipe member providing structural support; and a polyimide resin film less than ten microns thick formed on an inner surface of said hollow pipe member, said polyimide resin layer being transparent relative to said wavelength band of a transmission light of said optical hollow waveguide, wherein said polyimide resin layer includes 20 to 35 weight % of fluorine.

4. An optical hollow waveguide, comprising:

a hollow pipe member; and a polyimide resin layer formed on an inner surface of said hollow pipe member, said polyimide resin layer being transparent relative to a wavelength band of a transmission light of said optical hollow waveguide, wherein said polyimide resin layer comprises a plurality of polyimide resin layers, a dielectric layer being interposed between two adjacent layers of said plurality of polyimide resin layers, said dielectric layer being transparent relative to said wavelength band.

5. An optical hollow waveguide operational over a transmission wavelength band extending from ultraviolet to infrared light regions, comprising:

a hollow pipe member providing structural support; and a polyimide resin film less than ten microns thick formed on an inner surface of said hollow pipe member, and polyimide resin layer being transparent relative to said wavelength band of a transmission light of said optical hollow waveguide, wherein said hollow pipe member is of a metal selected from the group consisting of phosphorous bronze and stainless steel.

6. An optical hollow waveguide, comprising:

a hollow pipe member; and a polyimide resin layer formed on an inner surface of said hollow pipe member, said polyimide resin layer being transparent relative to a wavelength band of a transmission light of said optical hollow waveguide, said hollow pipe member being of a metal selected from the group consisting of phosphorous bronze and stainless steel, wherein said hollow pipe member has a metal thin film on an inner surface thereof, said metal thin film being of a metal different from said metal selected.

7. The hollow waveguide as defined in claim 6, wherein:

said metal thin film is of a metal selected from group consisting of gold, silver, molybdenum and nickel.

8. An optical hollow waveguide, comprising:

a hollow pipe member; and a polyimide resin layer formed on an inner surface of said hollow pipe member, said polyimide resin layer being transparent relative to a wavelength band of a transmission light of said optical hollow waveguide, wherein said hollow pipe member is of a non-metallic material selected from the group consisting of fluorine resin, silicon resin and glass, said hollow pipe member being coated with at least one metal thin film on an inner surface thereof.

9. The hollow waveguide as defined in claim 8, wherein:

said metal thin film is of a metal selected from the group consisting of gold, silver, molybdenum and nickel.

10. An optical hollow waveguide, comprising:

a hollow pipe member having a metal film at least on an inner surface thereof; and a polyimide resin layer formed on an inner surface of said metal film of said hollow pipe member, said polyimide resin layer being transparent relative to a wavelength band of a transmission light of said optical hollow waveguide, wherein said polyimide resin layer comprises a plurality of polyimide resin layers, a dielectric layer being interposed between two adjacent layers of said plurality of polyimide resin layers, said dielectric layer being transparent relative to said wavelength band.

11. An optical hollow waveguide operational over a transmission wavelength band extending from ultraviolet to infrared light regions, comprising:

a hollow pipe member providing structural support and having a metal film at least on an inner surface thereof; and a polyimide resin layer less than ten microns thick formed on an inner surface of said metal film of said hollow pipe member, said polyimide resin layer being transparent relative to said wavelength band of a transmission light of said optical hollow waveguide, wherein said hollow pipe member is of a metal selected from phosphorous bronze and stainless steel.

12. An optical hollow waveguide operational over a transmission wavelength band extending from ultraviolet to infrared light regions, comprising:

a hollow pipe member providing structural support; and a polyimide resin layer film less than ten microns thick formed on an inner surface of said hollow pipe member, and polyimide resin layer being transparent relative to a wavelength band of a transmission light of said optical hollow waveguide, and causing a low transmission loss for an infrared wavelength band of said transmission light.

13. An optical hollow waveguide, comprising:

a hollow pipe member; and a polyimide resin layer formed on an inner surface of said hollow pipe member, said polyimide resin layer being transparent relative to a wavelength band of a transmission light of said optical hollow waveguide, and causing a low transmission loss for transmission lights of wavelengths 2.9 µm, 5 µm and 10.6 µm.

14. An optical hollow waveguide, comprising a hollow pipe member; and a polyimide resin layer formed on an inner surface of said hollow pipe member, said polyimide resin layer being transparent relative to a wavelength band of a transmission light of said optical hollow waveguide, and said polyimide resin layer being formed by coating and hardening polyimide precursor on said inner surface of said hollow pipe member.

15. An optical hollow waveguide, comprising:

a hollow pipe member; and a polyimide resin layer formed on an inner surface of said hollow pipe member, said polyimide resin layer being transparent relative to a wavelength band of a transmission light of said optical hollow waveguide, and a thickness of said polyimide resin layer being less than 2.0 µm.

16. An optical hollow waveguide operational over a transmission wavelength band extending from ultraviolet to infrared light regions, comprising:

a hollow pipe member providing structural support and having a metal film at least on an inner surface thereof; and a polyimide resin layer less than ten microns thick formed on an inner surface of said metal film of said hollow pipe member, said polyimide resin layer being transparent relative to said wavelength band of a transmission light of said optical hollow waveguide, wherein said polyimide resin layer includes 20 to 35 weight % of fluoride.

* * * * *